United States Patent [19]

Duong et al.

[11] Patent Number: 5,895,754
[45] Date of Patent: Apr. 20, 1999

[54] NUCLEIC ACIDS ENCODING A TRUNCATED MOUSE β INTEGRIN SUBUNIT

[75] Inventors: Le T. Duong, Jenkintown; Gideon A. Rodan, Bryn Mawr; Elka M. Nutt, Lansdale, all of Pa.

[73] Assignee: Merck & Co., Inc., Rahway, N.J.

[21] Appl. No.: 08/960,387

[22] Filed: Oct. 29, 1997

Related U.S. Application Data

[62] Division of application No. 08/700,253, Aug. 20, 1996, abandoned

[60] Provisional application No. 60/003,020, Aug. 31, 1995.

[51] Int. Cl.$^6$ .................... C07H 21/04; C07K 14/78
[52] U.S. Cl. .................. 435/69.1; 435/320.1; 435/252.3; 435/325; 536/23.5; 935/9; 935/10; 935/11

[58] Field of Search .................... 435/69.1, 320.1, 435/252.3, 325; 536/23.5; 530/324, 350; 935/9–11

[56] References Cited

U.S. PATENT DOCUMENTS 5,661,005   8/1997   Shattil et al. .................... 435/69.1

*Primary Examiner*—Lorraine Spector
*Attorney, Agent, or Firm*—Joanne M. Giesser; Jack L. Tribble

[57] ABSTRACT

The full-length mouse β3 integrin has been cloned and sequenced. A new form of β3 integrin (β3 trunc) has also been cloned and sequenced.

4 Claims, 20 Drawing Sheets

```
  1  ATAACAATTT CACACAGGAA ACAGCTATGA CCATGATTAC GCCAAGCTCG
 51  AAATTAACCC TCACTAAAGG GAACAAAAGC TGGAGCTCCA CCGGTGGCGG
101  CCGCTCTAGA ACTAGTGGAT CCCCCGGGCT GCAGGAATTC GCGCCGTCGA
151  CGCGGCGGAC AGGATGCCAG CGCAGTGGCC GGGACAACTC TGGGCCGCTC
201  TGCTGGCGCT GGGGGCGCTG GCGGGCGTTG TTGTTGGAGA GTCCAACATC
251  TGTACCACAC GAGGCGTGAA CTCCTGCCAG CAGTGTCTGG CTGTGAGTCC
301  TGTGTGTGCC TGGTGCTCAG ATGAGACTTT GTCTCAGGGC TCACCCCGAT
351  GTAACCTGAA GGAGAACCTG CTGAAGGACA ATTGTGCTCC AGAGTCTATT
401  GAGTTCCCAG TCAGTGAGGC CCAGATCCTG GAGGCTAGGC CACTCAGCAG
451  CAAGGGCTCT GGAAGCAGCG CCCAGATCAC TCAAGTCAGC CCTCAGAGGA
501  TTGCCCTTCG ACTACGGCCA GATGATTCGA AGATCTTCTC ACTTCAAGTG
551  CGGCAGGTGG AGGATTACCC CGTGGACATC TACTACTTGA TGGACCTGTC
601  TTTCTCCATG AAGGATGATC TGTCCAGCAT CCAGACCCTG GGTACCAAGT
651  TGGCCTCTCA GATGCGCAAG CTTACTAGCA ACCTTCGGAT TGGCTTTGGG
```

FIG. 1A

```
 701  GCCTTCGTGG ACAAGCCTGT ATCGCCGTAC ATGTACATCT CCCCACCACA
 751  GGCAATCAAA AACCCCTGTT ACAATATGAA GAATGCCTGC TTGCCCATGT
 801  TTGGCTACAA ACACGTGCTG ACGCTAACCG ACCAGGTGTC CCGCTTCAAT
 851  GAAGAAGTGA AGAAACAGAG CGTGTCCCGT AATCGAGATG CCCAGAGGG
 901  CGGCTTTGAC GCCATCATGC AGGCTACAGT ATGTGATGAA AAAATTGGCT
 951  GGAGGAATGA CGCATCCCAT TTGCTAGTGT TTACCACGGA TGCCAAGACC
1001  CATATTGCCC TGGATGGAAG ACTGGCAGGC ATTGTCCTGC CCAATGATGG
1051  GCACTGTCAC ATTGGCACCG ACAACCACTA CTCTGCCCTC ACTACCATGG
1101  ACTACCCATC TCTGGGGCTG ATGACTGAGA AACTATCCCA GAAAAACATT
1151  AACTTGATCT TTGCAGTGAC TGAAAATGTC GTCAGCCTTT ACCAGAATTA
1201  TAGTGAGCTC ATTCCTGGA CCACAGTGGG AGTCCTGTCT GATGACTCAA
1251  GCAACGTCCT CCAGCTGATT GTTGATGCTT ACGGGAAAAT CCGCTCTAAA
1301  GTGGAGCTGG AAGTACGTGA CCTGCCGGAA GAACTGTCAC TGTCCTTCAA
1351  TGCCACCTGC CTCAACAACG AGTTATCCC GGGCCTCAAG TCTTGTGTGG
```

FIG. 1B

| | | | | |
|---|---|---|---|---|
| 1401 | GCCGCAAGAT | TGGAGACACG | GTGAGCTTTA | GTATCGAGGC | CAAGGTGCGT |
| 1451 | GGCTGCCCCC | AGGAGAAGGA | GCAGTCTTTC | ACTATCAAGC | CTGTGGGCTT |
| 1501 | TAAGGACAGC | CTCACCGTCC | AGGTGACCCT | CGACTGTGAC | TGTGCCTGCC |
| 1551 | AGGCCTTTGC | CCAGCCTTCC | AGCCCACGCT | GCAACAATGG | GAACGGGACT |
| 1601 | TTTGAGTGTG | GGGTGTGCCG | CTGTGACCAG | GGCTGGGCTGG | GGTCCATGTG |
| 1651 | TGAGTGCTCT | GAGGAGGATT | ACCGACCCTC | TCAGCAGGAA | GAGTGCAGCC |
| 1701 | CCAAGGAGGG | CCAGCCCATC | TGCAGCCAGC | CGACTTCGGC | CCTCTGTGGC |
| 1751 | CAGTGTGTCT | GCCATAGCAG | GACTTCTCCT | GCGTCCGCTA | GCAAGTACTG |
| 1801 | TGAGTGCGAT | GACTTCTCCT | GCGTCCGCTA | CAAAGGGGAG | ATGTGTTCCG |
| 1851 | GCCATGGGCA | ATGTAACTGT | GGGACTGCG | TGTGTGACTC | GGACTGGACT |
| 1901 | GGCTACTACT | GCAACTGTAC | TACACGCACT | GACACCTGCA | TGTCCACCAA |
| 1951 | TGGGCTGCTG | TGCAGCGGCC | GGGGCAACTG | CGAGTGCCGC | AGCTGTGTGT |
| 2001 | GCGTCCAGCC | AGGCTCCTAT | GGAGACACCT | GTGAGAAGTC | CCCCACCTGC |
| 2051 | CCAGATGCCT | GCTCCTTTAA | GAAGGAGTGT | GTGGAGTGTA | AGAAGTTCAA |

FIG. 1C

```
2101  CCGGGGAACG CTCCATGAAG AAAACACCTG CAGCCGCTAC TGCCGGGATG
2151  ACATCGAGCA GGTGAAAGAG CTGACGGATA CTGGCAAAAA CGCCGTGAAT
2201  TGTACCTACA AGAACGAGGA TGACTGTGTC GTCAGATTCC AGTACTACGA
2251  AGACACCAGT GGGAGGGCAG TCCTCTATGT GGTGGAAGAG CCTGAGTGTC
2301  CCAAGGGTCC TGATATCCTG TGGTACTGC TGTCAGTGAT GGGGGCCATC
2351  CTGCTCATTG GCCTTGCTAC TCTGCTCATC TGGAAGCTAC TCATCACCAT
2401  CCATGACCGG AAGGAATTTG CTAAATTTGA GGAAGAACGA GCCAGAGCTA
2451  AGTGGGACAC AGCAAACAAC CCGCTGTATA AGAGGCCAC CTCCACCTTC
2501  ACCAATATCA CGTACCGAGG AACTTAATGA
```

FIG. 1D

```
  1  ATAACAATTT CACACAGGAA ACAGCTATGA CCATGATTAC GCCAAGCTCG
 51  AAATTAACCC TCACTAAAGG GAACAAAAGC TGGAGCTCCA CCGGTGGCGG
101  CCGCTCTAGA ACTAGTGGAT CCCCCGGGCT GCAGGAATTC GCGCCGTCGA
151  CGCGGGCGGAC AGGATGCGAG CGCAGTGGCC GGGACAACTC TGGGCCGCTC
201  TGCTGGCGCT GGGGGGCGCTG GCGGGGCGTTG TTGTTGGAGA GTCCAACATC
251  TGTACCACAC GAGGCGTGAA CTCCTGCCAG CAGTGTCTGG CTGTGAGTCC
301  TGTGTGTGCC TGGTGCTCAG ATGAGACTTT GTCTCAGGGC TCACCCGAT
351  GTAACCTGAA GGAGAACCTG CTGAAGGACA ATTGTGCTCC AGAGTCTATT
401  GAGTTCCCAG TCAGTGAGGC CCAGATCCTG GAGGCTAGGC CACTCAGCAG
451  CAAGGGCTCT GGAAGCAGCG CCCAGATCAC TCAAGTCAGC CCTCAGAGGA
501  TTGCCCTTCG ACTACGGCCA GATGATTCGA AGATCTTCTC ACTTCAAGTG
551  CGGCAGGTGG AGGATTACCC CGTGGACATC TACTACTTGA TGGACCTGTC
601  TTTCTCCATG AAGGATGATC TGTCCAGCAT CCAGACCCTG GGTACCAAGT
651  TGGCCTCTCA GATGCGCAAG CTTACTAGCA ACCTTCGGAT TGGCTTTGGG
```

FIG. 2A

```
 701  GCCTTCGTGG ACAAGCCTGT ATCGCCGTAC ATGTACATCT CCCCACCACA
 751  GGCAATCAAA AACCCCTGTT ACAATATGAA GAATGCCTGC TTGCCCATGT
 801  TTGGCTACAA ACACGTGCTG ACGCTAACCG ACCAGGTGTC CCGCTTCAAT
 851  GAAGAAGTGA AGAAACAGAG CGTGTCCCGT AATCGAGATG CCCCAGAGGG
 901  CGGCTTTGAC GCCATCATGC AGGCTACAGT ATGTGATGAA AAAATTGGCT
 951  GGAGGAATGA CGCATCCCAT TTGCTAGTGT TTACCACGGA TGCCAAGACC
1001  CATATATTGCCC TGGATGGAAG ACTGGCAGGC ATTGTCCTGC CCAATGATGG
1051  GCACTGTCAC ATTGGCACCG ACAACCACTA CTCTGCCCTC ACTACCATGG
1101  ACTACCCATC TCTGGGGCTG ATGACTGAGA AACTATCCCA GAAAAACATT
1151  AACTTGATCT TTGCAGTGAC TGAAAATGTC GTCAGCCTTT ACCAGAATTA
1201  TAGTGAGCTC ATTCCTGGGA CCACAGTGGG AGTCCTGTCT GATGACTCAA
1251  GCAACGTCCT CCAGCTGATT GTTGATGCTT ACGGGAAAAT CCGCTCTAAA
1301  GTGGAGCTGG AAGTACGTGA CCTGCCGGAA GAACTGTCAC TGTCCTTCAA
1351  TGCCACCTGC CTCAACAACG AGGTTATCCC GGGCCTCAAG TCTTGTGTGG
```

FIG. 2B

```
1401  GCCGCAAGAT TGGAGACACG GTGAGCTTTA GTATCGAGGC CAAGGTGCGT
1451  GGCTGCCCCC AGGAGAAGGA GCAGTCTTTC ACTATCAAGC CTGTGGGCTT
1501  TAAGGACAGC CTCACCGTCC AGGTGACCTT CGACTGTGAC TGTGCCTGCC
1551  AGGCCTTTGC CCAGCCTTCC AGCCCACGCT GCAACAATGG GAACGGGACT
1601  TTTGAGTGTG GGGTGTGCCG CTGTGACCAG GGCTGGCTGG GGTCCATGTG
1651  TGAGTGCTCT GAGGAGGATT ACCGACCCTC TCAGCAGGAA GAGTGCAGCC
1701  CCAAGGAGGG CCAGCCCATC TGCAGCCAGC GGGAGAGAGTG CCTCTGTGGC
1751  CAGTGTGTCT GCCATAGCAG CGACTTCCGC GGTCCGGCTA AGATCACTCG GCAAGTACTG
1801  TGAGTGCGAT GACTTCTCCT GCGTCCGGCTA CAAAGGGGAG ATGTGTTCCG
1851  GCCATGGGCA ATGTAACTGT GGGACTGCGC TGTGTGACTC GGACTGGACT
1901  GGCTACTACT GCAACTGTAC TACACGCACT GACACCTGCA TGTCCACCAA
1951  TGGGCTGCTG TGCAGCGGCC GGGGCAACTG CGAGTGCGGC AGCTGTGTGT
2001  GCGTCCAGCC AGCTCCTAT GGAGACACCT GTGAGAAGTG CCCCACCTGC
2051  CCAGATGCCT GCTCCTTTAA GAAGGAGTGT GTGGAGTGTA AGAAGTTCAA
```

FIG. 2C

```
2101  CGGGGAACG CTCCATGAAG AAAACACCTG CAGCCGCTAC TGCCGGGATG
2151  ACATCGAGCA GGTGAAAGAG CTGACGGATA CTGGCAAAAA CGCCCGCGGC
2201  CGCGTCGACT GGAGACTCAC GGAGCATGAC ATACTCACCT GTCACCTATT
2251  TAGAAGACTG AGGCAGGAAG ATAAGTTTCT GGACAGCCTA GTCTGCATAA
2301  AGACCACCCT GTCTCAAAAA GCATAAAAGG GGCGTGGTGA ATGCCCTGCTT
2351  AGCATATAGC CCTTGGTTGC AGGTAGTGCA GTACATAGGT GAAATCTGCC
2401  GCTACCTGCT GAGGCAGCCG GTTCGCGACG TGGAGCAGCG ACACCGCGTG
2451  CGCCTGCCCG CGGGTAATGG GCTGCGGGCCA GCCATCTGGG AGGAGTTCAC
2501  GCAGCGCTTC GGTGTGCCAC AGATCGGCGA GTTCTACGGC GCTACCGAGT
2551  GCAACTGAGC ATTGCCAACA TGGACGGCAA GGTTCGCAGC TGTGGGGTGC
2601  AGGCGGGGCG TGTCGGTTTC CTACGACACA AGAGCCTTCA GGCCCGCCCTC
2651  ACCGCCGCTG TATTCACCCT AGGTCGGCTC CTGCGGCTTC AACAGCCGTA
2701  TCCTCACGCA TGTGTACCCC ATCCGTCTGG TCAAGGTCAA TGAGGACACG
2751  ATGGAGCCAC TGCGGGACTC CGAGGGCCTC TGCATCCCGT GCCAGCCCGG
```

FIG. 2D

```
2801  TGAGTGTGGC CCTTGCCTGG TGCCTCGGGG AGCTAGAGTC CCCACGGCCC
2851  CCACACCCAC TCAGCTTGAG TGTCAACCTC CTTCCAGGGG AACCCGGCCT
2901  TTCGTGGGCC AGATCAACCA GCAGGACCCT CTGCGGCGTT TCGATGGTTA
2951  TGTTAGTGAC AGTGCCACCA ACAAGAAGAT TGCCCACAGC GTTTTCCGAA
3001  AGCCGATACG gCCTACCTCT CAGGTGCGGA CGCTCGTGGT CGTGGCTGGG
3051  CTGGCTGTCA GACTGCAAAG CCCGGTCCCA TCTGCCCCTC TTCCCTGCAG
3101  GTGACGTGCT AGTGATGGAC GAGCTGGGCT ACATGTATTT CCGTGACCGC
3151  AGCGGGACA CCTTCCGCTG GCGCGGGAGA ACGTGTCCAA CCACGGAGGT
3201  GAAGCCCGTG CTGAGCCGCC TACTGGGCCA GACGGACGTG GCTGTGTATG
3251  GGGTGGCTGT GCAGGCAAGC TGGGGACACA GAAGGGACCT GGTGGTTGT
3301  AGCCCCATGG AGTCCATCCA GAAGGACCT GCAGGTACAG TACCCGTGGG
3351  CCATGCACAA GGTGGAGAAC TGTGTTGCTG CTGACTGGGT GGGCACTGGG
3401  TTGGAATCC ATCACACATTC CTAATATTGA ACTTCAGTCT GGGGGACCCC
3451  TTCTCAGGAT CAGAAGGCTG AAAACAGGTC GACGCCGCCC GGAATTCGAT
3501  ATCAAGCTTA TCGATCC
```

FIG. 2E

```
1    *QFHTGNSYD HDYAKLEINP H*REQKLELH RWRPL*N*WI PRAAGIRAVD
51   AADRMRAQWP GQLWAALLAL GALAGVVVGE SNICTTRGVN SCQQCLAVSP
101  VCAWCSDETL SQGSPRCNLK ENLLKDNCAP ESIEFPVSEA QILEARPLSS
151  KGSGSSAQIT QVSPQRIALR LRPDDSKIFS LQVRQVEDYP VDIYYLMDLS
201  FSMKDDLSSI QTLGTKLASQ MRKLTSNLRI GFGAFVDKPV SPYMYISPPQ
251  AIKNPCYNMK NACLPMFGYK HVLTLTDQVS RFNEEVKKQS VSRNRDAPEG
301  GFDAIMQATV CDEKIGWRND ASHLLVFTTD AKTHIALDGR LAGIVLPNDG
351  HCHIGTDNHY SASTTMDYPS LGLMTEKLSQ KNINLIFAVT ENVVSLYQNY
401  SELIPGTTVG VLSDDSSNVL QLIVDAYGKI RSKVELEVRD LPEELSLSFN
451  ATCLNNEVIP GLKSCVGRKI GDTVSFSIEA KVRGCPQEKE QSFTIKPVGF
501  KDSLTVQVTF DCDCACQAFA QPSSPRCNNG NGTFECGVCR CDQGWLGSMC
551  ECSEEDYRPS QQEECSPKEG QPICSQRGEC LCGQCVCHSS DFGKITGKYC
601  ECDDFSCVRY KGEMCSGHGQ CNCGDCVCDS DWTGYYCNCT TRTDTCMSTN
651  GLLCSGRGNC ECGSCVCVQP GSYGDTCEKC PTCPDACSFK KECVECKKFN
```

FIG. 3A

```
 701  RGTLHEENTC  SRYCRDDIEQ  VKELTDTGKN  ARGRVDWRLT  EHDILTCHLF
 751  RRLRQEDKFL  DSLVCIKTTL  SQKA*KGRGE  CLLSI*PLVA  GSAVHR*NLP
 801  LPAEAAGSRR  GAATPRAPGR  G*WAAASHLG  GVHAALRCAT  DRRVLRRYRV
 851  QLSIANMDGK  VRSCGVQAGA  VGFLRHKSLQ  AALTAAVFTL  GRLLRLQQPY
 901  PHACVPHPSG  QGQ*GHDGAT  AGLRGPLHPV  PAR*VWPLPG  ASGS*SPHGP
 951  HTHSA*VSTS  FQGNPAFRGP  DQPAGPSAAF  RWLC**QCHQ  QEDCPQRFPK
1001  GDTAYLSGAD  ARGRGWAGCQ  TAKPGPICPS  SLQVTC**WT  SWATCISVTA
1051  AGTPSAGAGE  RVQPRR*SRC  *AAYWARRTW  LCMGWLCRQA  GDTGWLWCAG
1101  APWSPSRRDL  QVQYPWAMHK  VENCVAADWV  GTGLGIHPHS  *Y*TSVWGTP
1151  SQDQKAENRS  TPPGIRYQAY  RS
```

FIG. 3B

```
  1  *QFHTGNSYD HDYAKLEINP H*REQKLELH RWRPL*N*WI PRAAGIRAVD
 51  AADRMRAQWP GQLWAALLAL GALAGVVVGE SNICTTRGVN SCQQCLAVSP
101  VCAWCSDETL SQGSPRCNLK ENLLKDNCAP ESIEFPVSEA QILEARPLSS
151  KGSGSSAQIT QVSPQRIALR LRPDDSKIFS LQVRQVEDYP VDIYYLMDLS
201  FSMKDDLSSI QTLGTKLASQ MRKLTSNLRI GFGAFVDKPV SPYMYISPPQ
251  AIKNPCYNMK NACLPMFGYK HVLTLTDQVS RFNEEVKKQS VSRNRDAPEG
301  GFDAIMQATV CDEKIGWRND ASHLLVFTTD AKTHIALDGR LAGIVLPNDG
351  HCHIGTDNHY SASTTMDYPS LGLMTEKLSQ KNINLIFAVT ENVVSLYQNY
401  SELIPGTTVG VLSDDSSNVL QLIVDAYGKI RSKVELEVRD LPEELSLSFN
451  ATCLNNEVIP GLKSCVGRKI GDTVSFSIEA KVRGCPQEKE QSFTIKPVGF
501  KDSLTVQVTF DCDCACQAFA QPSSPRCNNG NGTFECGVCR CDQGWLGSMC
551  ECSEEDYRPS QQEECSPKEG QPICSQRGEC LCGQCVCHSS DFGKITGKYC
601  ECDDFSCVRY KGEMCSGHGQ CNCGDCVCDS DWTGYYCNCT TRTDTCMSTN
651  GLLCSGRGNC ECGSCVCVQP GSYGDTCEKC PTCPDACSFK KECVECKKFN
```

FIG. 4A

701 RGTLHEENTC SRYCRDDIEQ VKELTDTGKN AVNCTYKNED DCVVRFQYYE
751 DTSGRAVLYV VEEPECPKGP DILVVLLSVM GAILLIGLAT LLIWKLLITI
801 HDRKEFAKFE EERARAKWDT ANNPLYKEAT STFTNITYRG T**

FIG. 4B

```
      55                  .              .              .              .              .
MRAQWPGQLWAALLALGALAGVVVGESNICTTRGVNSCQQCLAVSPVCAW 104

|||||||||||||||||||||||||||||||||||||||||||||||||
      55
MRAQWPGQLWAALLALGALAGVVVGESNICTTRGVNSCQQCLAVSPVCAW 104

.                 .              .              .
     105
CSDETLSQGSPRCNLKENLLKDNCAPESIEFPVSEAQILEARPLSSKGSG 154

|||||||||||||||||||||||||||||||||||||||||||||||||
     105
CSDETLSQGSPRCNLKENLLKDNCAPESIEFPVSEAQILEARPLSSKGSG 154

.              .              .
     155
SSAQITQVSPQRIALRLRPDDSKIFSLQVRQVEDYPVDIYYLMDLSFSMK 204

|||||||||||||||||||||||||||||||||||||||||||||||||
     155
SSAQITQVSPQRIALRLRPDDSKIFSLQVRQVEDYPVDIYYLMDLSFSMK 204

.                    .              .              .
     205
DDLSSIQTLGTKLASQMRKLTSNLRIGFGAFVDKPVSPYMYISPPQAIKN 254

|||||||||||||||||||||||||||||||||||||||||||||||||
     205
DDLSSIQTLGTKLASQMRKLTSNLRIGFGAFVDKPVSPYMYISPPQAIKN 254

.              .              .
     255
PCYNMKNACLPMFGYKHVLTLTDQVSRFNEEVKKQSVSRNRDAPEGGFDA 304

|||||||||||||||||||||||||||||||||||||||||||||||||
     255
PCYNMKNACLPMFGYKHVLTLTDQVSRFNEEVKKQSVSRNRDAPEGGFDA 304
```

FIG. 5A

```
      305
IMQATVCDEKIGWRNDASHLLVFTTDAKTHIALDGRLAGIVLPNDGHCHI 354
|||||||||||||||||||||||||||||||||||||||||||||||||
      305
IMQATVCDEKIGWRNDASHLLVFTTDAKTHIALDGRLAGIVLPNDGHCHI 354

355
GTDNHYSASTTMDYPSLGLMTEKLSQKNINLIFAVTENVVSLYQNYSELI 404
|||||||||||||||||||||||||||||||||||||||||||||||||
      355
GTDNHYSASTTMDYPSLGLMTEKLSQKNINLIFAVTENVVSLYQNYSELI 404

405
PGTTVGVLSDDSSNVLQLIVDAYGKIRSKVELEVRDLPEELSLSFNATCL 454
|||||||||||||||||||||||||||||||||||||||||||||||||
      405
PGTTVGVLSDDSSNVLQLIVDAYGKIRSKVELEVRDLPEELSLSFNATCL 454

455
NNEVIPGLKSCVGRKIGDTVSFSIEAKVRGCPQEKEQSFTIKPVGFKDSL 504
|||||||||||||||||||||||||||||||||||||||||||||||||
      455
NNEVIPGLKSCVGRKIGDTVSFSIEAKVRGCPQEKEQSFTIKPVGFKDSL 504

505
TVQVTFDCDCACQAFAQPSSPRCNNGNGTFECGVCRCDQGWLGSMCECSE 554
|||||||||||||||||||||||||||||||||||||||||||||||||
      505
TVQVTFDCDCACQAFAQPSSPRCNNGNGTFECGVCRCDQGWLGSMCECSE 554
```

FIG. 5B

```
      555
EDYRPSQQEECSPKEGQPICSQRGECLCGQCVCHSSDFGKITGKYCECDD 604
      |||||||||||||||||||||||||||||||||||||||||||||||||
      555
EDYRPSQQEECSPKEGQPICSQRGECLCGQCVCHSSDFGKITGKYCECDD 604

605
FSCVRYKGEMCSGHGQCNCGDCVCDSDWTGYYCNCTTRTDTCMSTNGLLC 654
      |||||||||||||||||||||||||||||||||||||||||||||||||
      605
FSCVRYKGEMCSGHGQCNCGDCVCDSDWTGYYCNCTTRTDTCMSTNGLLC 654

655
SGRGNCECGSCVCVQPGSYGDTCEKCPTCPDACSFKKECVECKKFNRGTL 704
      |||||||||||||||||||||||||||||||||||||||||||||||||
      655
SGRGNCECGSCVCVQPGSYGDTCEKCPTCPDACSFKKECVECKKFNRGTL 704

705
HEENTCSRYCRDDIEQVKELTDTGKNAVNCTYKNEDDCVVRFQYYEDTSG 754
      |||||||||||||||||||||||||||           .|:...|..
      705
HEENTCSRYCRDDIEQVKELTDTGKNA.........RGRVDWRLTEHDIL 745

755 RAVLYVVEEPECPKGPDILVVLLSVMGA 782
       .|:   .| .|  | ||.: ..::.
   746 TCHLFRRLRQE.DKFLDSLVCIKTTLSQ 772
```

FIG. 5C

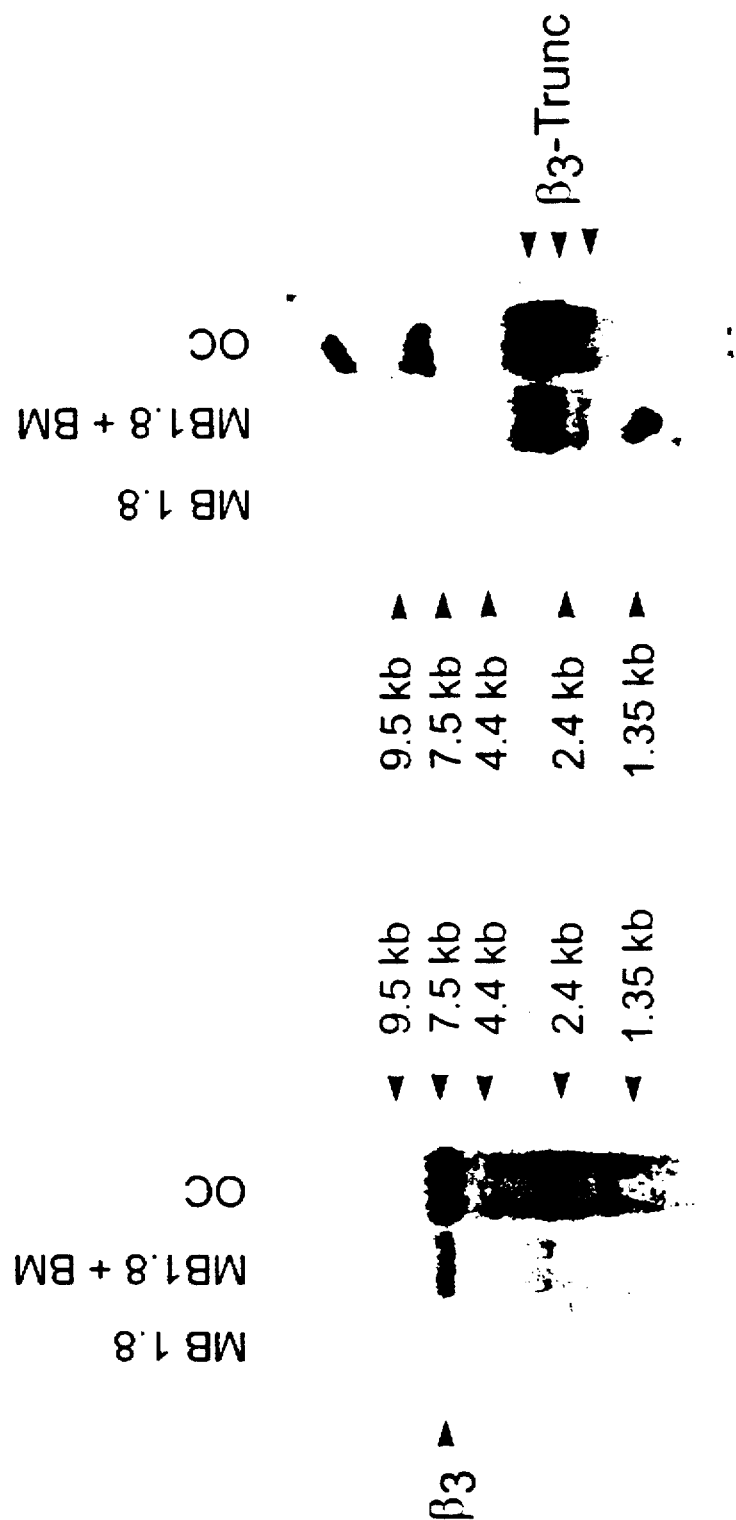

5,895,754

1

NUCLEIC ACIDS ENCODING A TRUNCATED MOUSE β INTEGRIN SUBUNIT

This is a division of application Ser. No. 08/700,253, filed Aug. 20, 1996, now abandoned, which claims the benefit of U.S. provisional application No. 60/003,020, filed Aug. 31, 1995.

DESCRIPTION OF THE INVENTION:

This invention relates to a new mouse vitronectin receptor subunit β3 (β3-trunc), the full length mouse vitronectin receptor, their nucleic acids, and to assays using these receptors. Additionally this invention includes soluble integrins which lack transmembrane and cytoplasmic domains.

BACKGROUND OF THE INVENTION

Integrins are transmembrane glycoproteins that mediate cell-cell and cell-matrix interactions. They contain two subunits, α and β, which are joined in a non-covalent complex. There are numerous α and β subunits known. Alpha subunits show some homology with other alpha subunits and beta subunits tend to show homology with other beta subunits, however, the alpha subunits tend to be quite distinct from beta subunits.

Osteoclasts are the primary cells responsible for bone resorption. Osteoclasts migrate to the area of the bone to be absorbed, and then attach to the bone. Adhesion molecules, including integrins, are believed to be involved in the processes of migration and attachment.

Recent studies have shown that both mature osteoclasts and tissue culture generated osteoclast-like cells highly express the vitronectin integrin receptor $\alpha_v\beta_3$. The $\alpha_v\beta_3$ integrin receptor recognizes the tripeptide Arg-Gly-Asp (RGD), found in many bone matrix proteins, and thus is thought to be involved in the attachment processes. However, there is no direct evidence that $\alpha_v\beta_3$ mediates osteoclast attachment to bone in vivo.

Partial sequence of the mouse β3 cDNA was previously reported by Cieutat, et al., 1993 Biochem. Biophys. Res. Comm. 193:771–778. Cieutat et al., cloned β3 from mouse kidney RNA using RT/PCR and human primers. This published sequence did not have the N-terminus and the last 4 amino acids at the C-terminus.

There are presently two types of screens for the $\alpha_v\beta_3$ ligands as an inhibitor for bone resorption: a binding assay based on human recombinant $\alpha_v\beta_3$ integrin and a functional assay based on rodent osteoclasts. To exclude the possibility of species-based potency differences in ligand interaction with the $\alpha_v\beta_3$ integrin, it would be desirable to develop an assay which uses the β3 integrin subunit from a mouse osteoclast.

DETAILED DESCRIPTION OF THE INVENTION

This invention relates to the full length mouse β3 integrin subunit (β3), nucleic acids encoding it, and to processes for cloning it. Another aspect of this invention is a novel form of the β3 integrin subunit, referred to as β3-trunc, which lacks the transmembrane and cytoplasmic domains, to nucleic acids encoding it, and to processes for producing it. Another aspect of this invention is the use of these integrins in assays to identify novel compounds which inhibit the bone absorption process.

Yet another aspect of this invention is a soluble ligand binding integrin which, like other soluble receptors, sup-

2 presses the interaction of the full length integrins with their ligands. The main signal transduction pathway mediated by the a membrane bound integrin is transduced through the cytoplasmic domain of the β subunit. A soluble receptor, which has an intact binding domain but lacks the cytoplasmic domain, will suppress or compete with the normal signals mediated by the wild type receptor.

BRIEF DESCRIPTION OF THE FIGURES

FIGS. 1A-C. is the complete sequence of the mouse β3 integrin (2.3 kb) cloned from a osteoclast cDNA library. The "ATG" initiation codon begins at position 164 and both a "TAA" and a "TGA" stop codons are seen starting at position 2525.

FIGS. 2A-D is the cDNA of the mouse β3-trunc. The "ATG" initiation codon begins at position 164.

FIG. 3 is the amino acid sequence of mouse β3-trunc. This sequence shows the corresponding amino acids, including untranslated regions. Asterisks denote stop codons. As shown in FIG. 5, the open reading frame begins with the "Met" at position 55, and ends with the "Ala" at position 782.

FIG. 4 is the amino acid sequence of the full-length mouse β3. This sequence shows corresponding amino acids, including untranslated regions. Asterisks denote stop codons. As shown in FIG. 5, the open reading frame begins with the "Met" at position 55, and ends with the "Thr" at position 841.

FIGS. 5A-D is an amino acid sequence comparison between the mouse full-length β3 (top line) and the mouse β3-trunc (lower line).

FIG. 6 are gels showing the expression of mouse full-length β3 and β3-trunc in osteoclast-like cells in the mouse co-culture system.

Figure 7:
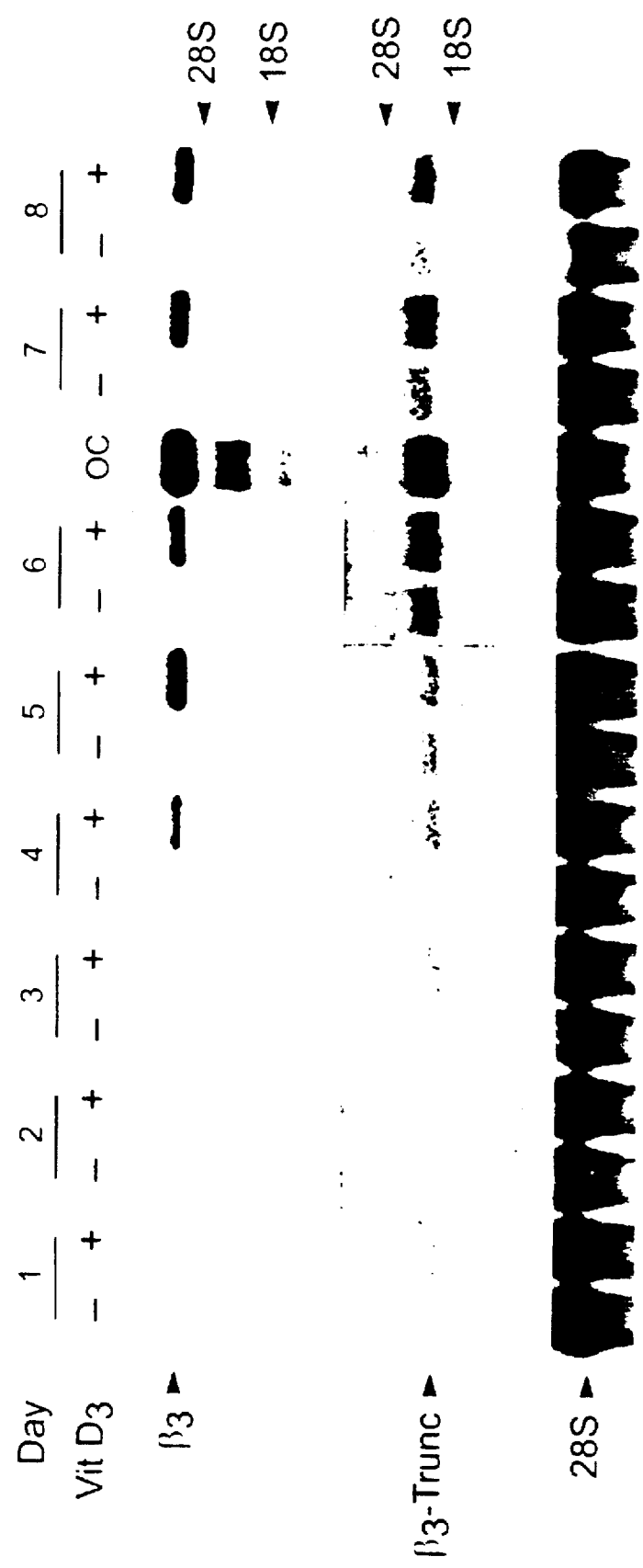
FIG. 7 are gels demonstrating the regulation of both β3 and β3-trunc by 1,25-dihydroxy Vitamin $D_3$.

As used in the specification and claims, the following definitions shall apply:

"Free from associated mouse nucleic acid"—physically separated from mouse nucleic acid (DNA or RNA) which is not either (i) mouse β3 nucleic acid or (ii) mouse β3-trunc nucleic acid.

"Free from associated mouse DNA"—physically separated from mouse DNA which is not either (i) mouse DNA encoding β3 integrin or (ii) DNA encoding truncated β3 integrin.

"Substantially pure"—a protein or nucleic acid is "substantially pure" when the amount of other protein or nucleic acid present in a sample is less than about 5% of the sample by weight.

Thus one aspect of this invention is nucleic acids which encode the full length mouse β3 integrin, said nucleic acid being free from associated mouse nucleic acid. Preferably the nucleic acid is a DNA. A preferred type of DNA is cDNA, and a particularly preferred cDNA is that shown in FIG. 1.

Partial sequence of the mouse β3 cDNA was previously reported by Cieutat, et al., 1993 Biochem. Biophys. Res. Comm. 193:771–778, which is hereby incorporated by reference. Cieutat et al cloned β3 from mouse kidney RNA using RT/PCR and human primers. This published sequence did not have the N-terminus and the last 4 amino acids at the C-terminus. One aspect of this invention comprises a complete sequence of the mouse β3 integrin (2.3 kb) cloned from a osteoclast cDNA library, free from associated mouse cDNA or which is substantially pure. This is presented in FIG. 1. The sequence of β3 was derived from the cDNA sequence of clone 9A (from 5'-end to base 2028) and the PCR sequence of a fragment encoding the last 363 bases at the 3'-end.

Another aspect of this invention is the complete, full-length β3 peptide, free from associated mouse peptides, or substantially pure which is shown in FIG. 4. Substantially pure mouse full-length β3 is another aspect of this invention.

Mouse β3 shows 86% homology with the human β3 at the DNA level, 90% overall homology in the amino acid sequence, 90% and 100% homology in the ligand binding domains (residues 109–171 and residues 204–229, respectively). 97% homology in the transmembrane domain and 100% identity in the cytoplasmic tail. This high homology is consistent with the quantitative similarity in the binding of ligands to human and mouse αvβ3.

Another aspect of this invention are vectors which comprise the full length mouse β3 nucleic acids, preferably cDNA and to host cells transformed with these vectors. Preferred host cells are embryonic kidney cells. This invention also includes the method of making full length β3 by transforming a host cell with a vector comprising full length mouse β3 DNA and harvesting the β3 so produced.

Characterization of the truncated mouse β3 cDNA (β3-trunc)

Another aspect of this invention is nucleic acids which encode a truncated mouse β3 (β3-trunc) peptide, free from associated mouse nucleic acids, or which are substantially pure. A preferred form of β3-trunc DNA is cDNA; a particularly preferred cDNA is that shown in FIG. 2.

Figure 9:
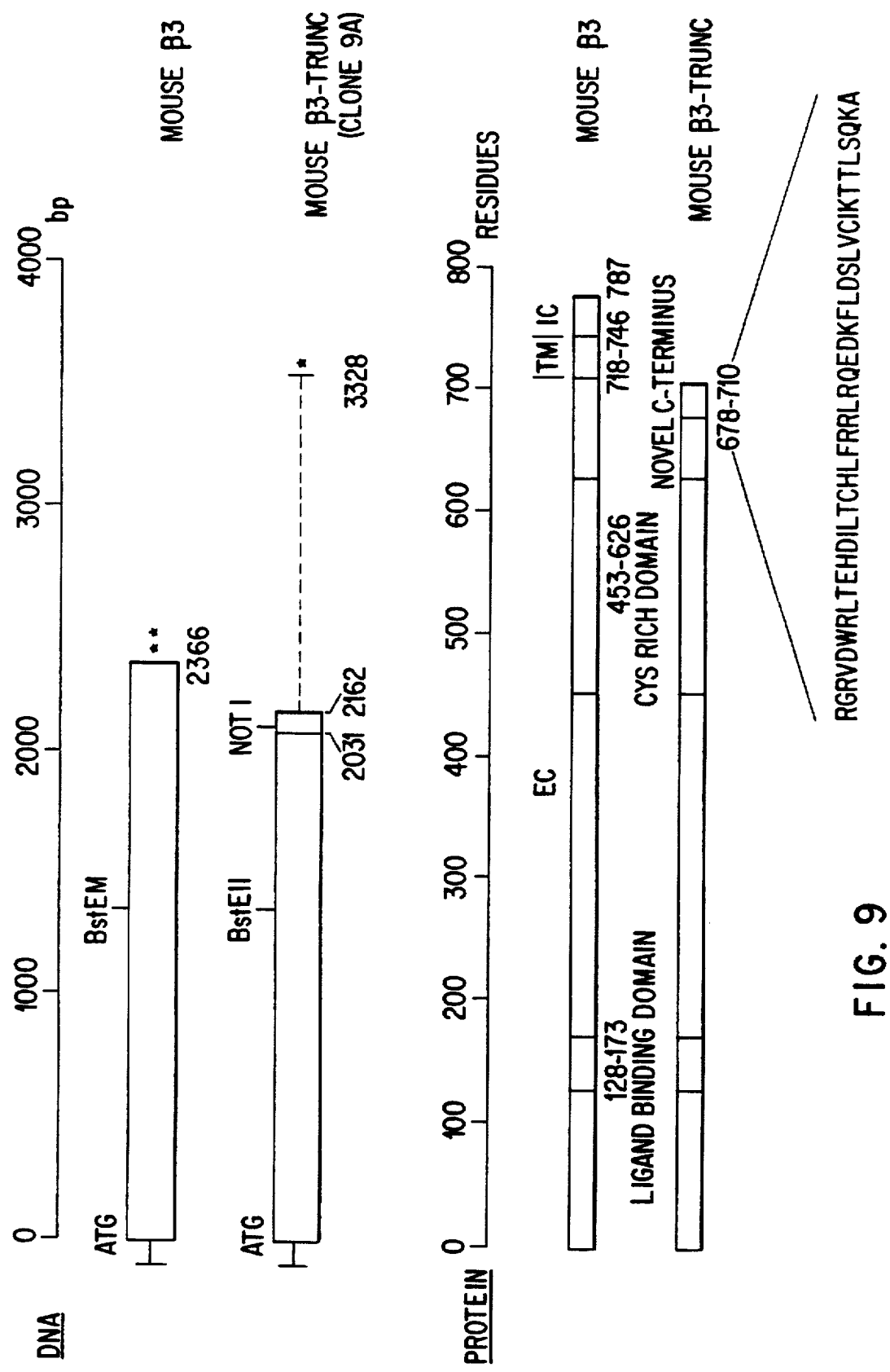
FIG. 9 are diagrams of the mouse β3 and β3-trunc genes and the proteins encoded.

Another aspect of this invention is the β3-trunc peptide, free from associated mouse peptides, or substantially pure. This is shown in FIG. 3 and FIG. 9. Mouse β3-trunc, which includes 5'-untranslated region (163 bp), 5'-coding region of the extracellular domain of β3 (up to base 2028 or residue 676) and a diversed 3'-coding region. Interestingly, the diversed 3'-coding region includes an inframe addition of 43 amino acids, followed by a long 3'-untranslated sequence (1.2 kb). From homology analysis, this diversed 3'-sequence shows no significant homology with any known gene. The protein encoded by the β3-trunc gene contains the entire ligand binding and cysteine-rich domains, but lacks the transmembrane and cytoplasmic domains.

The expression of β3-trunc and its regulation in the co-culture-derived osteoclasts was investigated. Northern analysis of the co-culture, with either a 5'-probe or a 3'-specific β3-trunc probe, reveals that the osteoblastic MB 1.8 cells do not express β3 or β3-trunc (see FIG. 6). However, the expression of both forms is highly enriched in the partially purified preparation of osteoclasts from the co-culture. The 5'-probe hybridizes to a major mRNA product at 6.5 kb and several minor forms of 2–4 kb. The β3-trunc specific probe detects a major mRNA product at 3 kb and two minor mRNA products at 2 and 4 kb. Generation of osteoclasts in the co-culture system depends on the presence of 1,25-dihydroxy Vitamin $D_3$ (1,25(OH)2D3). Both forms of β3 integrin were up-regulated by 1,25(OH)2D3 treatment of the co-culture system as shown in FIG. 7.

Figure 8:
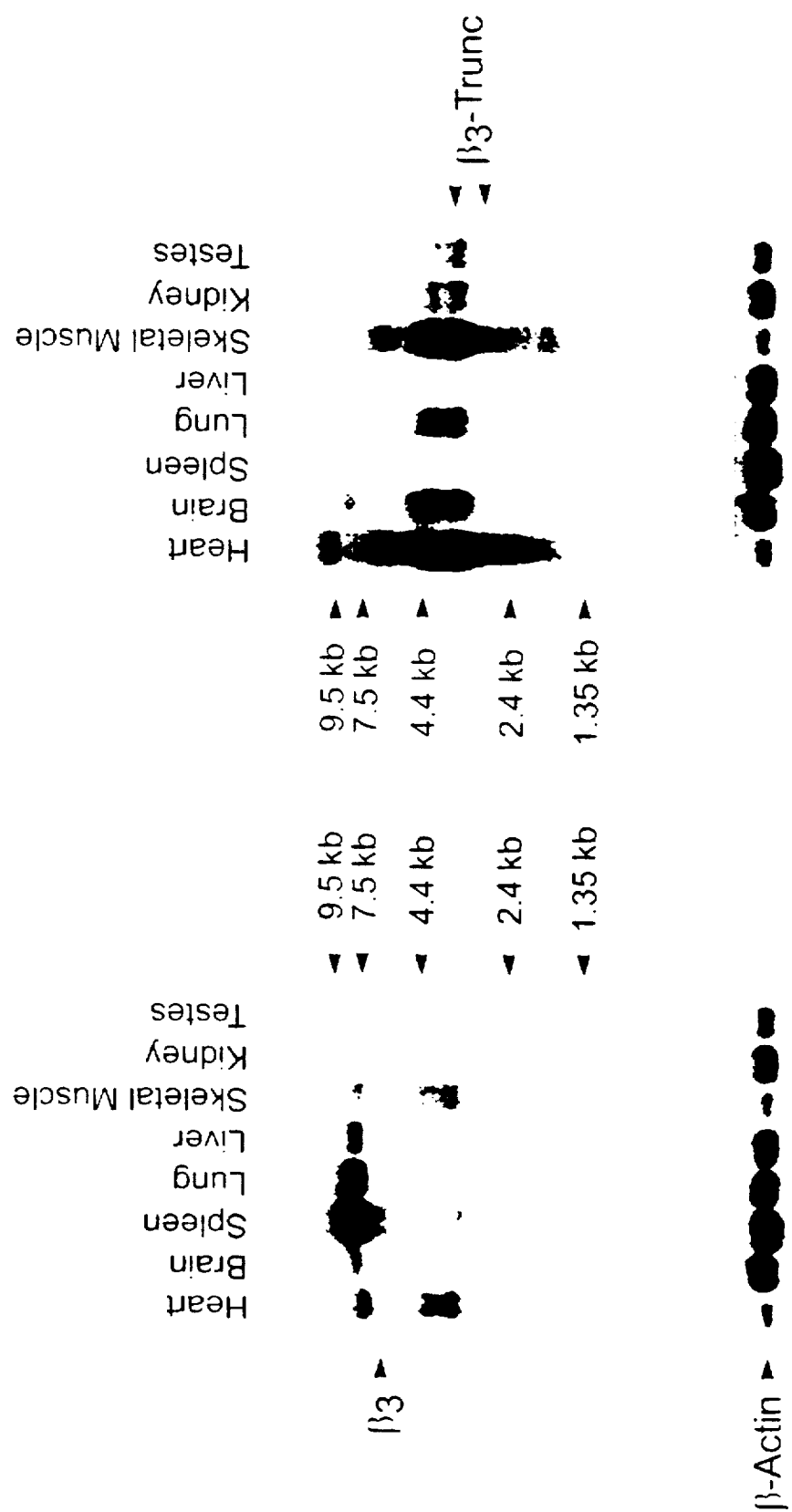
FIG. 8 are gels showing the expression of β3 and β3-trunc in various tissues.

Murine tissue distribution reveals different patterns of expression for β3 and β3-trunc. This is demonstrated in FIG. 8. Full length β3 is expressed in spleen>lung>liver, with a very minor amount of β3 messages (6.5 kb) detected in other tissues. In contrast, β3-trunc (2–4 kb) messages are expressed in heart>skeletal muscle>brain>lung.

Since β3-trunc lacks the transmembrane and cytoplasmic domains, it can be considered a soluble ligand binding integrin. This represents the first such soluble integrin. Thus another aspect of this invention is an integrin which lacks the transmembrane and cytoplasmic domains. Such an integrin is able to circulate throughout the organism. Its physiological role appears to be suppression of the signaling pathway mediated by the full length β3 integrins interaction with their ligands. Integrin-ligand signals are generally transmitted to the cytoplasm by a mechanism involving the cytoplasmic domain. However, when a ligand binds to β3-trunc, which lacks such a domain, the signal would not reach the cytoplasm. Therefore, the soluble ligands can act as negative regulators, tying up ligand without signaling the cell.

Assays

Another aspect of this invention are novel assays. The novel assays of this invention are to identify inhibitors of human ($\alpha_v\beta_3$) receptors. Such inhibitors would be useful in a variety of disease conditions including diseases associated with bone resorption such as osteoporosis. Generally, potential inhibitors are first screened for their ability to bind to recombinant human $\alpha_v\beta_3$ receptors using an assay such as the one set forth in Example 2. Further in vitro testing of the potential inhibitor, however, generally occurs using mouse or other rodent cell systems. It is not uncommon for the same potential inhibitor to display different responses in the two systems, and until now the investigator would not be able to determine if the differences were due to the effect of the different species' receptors or to actual in vitro activity.

Thus, in one aspect of this invention, a potential inhibitor to osteoclast formation is placed into contact with either mouse full length β3 or mouse β3-trunc, and its ability to bind is measured. The binding may be measured by any known means, such as by measuring the displacement of a compound known to bind to β3, such as echistatin. This information can be used to better assess the activity of the potential inhibitor in an in vitro assay.

By means of example only, if a potential inhibitory compound were found to bind well to human $\alpha_v\beta_3$ in the recombinant $\alpha_v\beta_3$ assay, but exhibited less inhibitory activity than expected in the mouse in vitro assay, one could determine whether the decrease in expected activity was due to the compound's inability to bind efficiently to the mouse integrin or whether the decreased activity was a true reflection of the compound's in vitro activity, by performing a mouse β3 or β3-trunc assay.

The following non-limiting Examples are presented to further illustrate the invention.

EXAMPLES

General techniques

First-Strand cDNA synthesis kit and QuickPrep mRNA Purification Kit were from Pharmacia. Lamda ZAP II cloning kits were from Stratagene. Mouse tissue mRNA blots were purchased from Clontech. Hybond-N filters were from Amersham. Restriction enzymes were from various sources: BioLabs, Promega and Stratagene. Tissue culture media were from Gibco. Fetal bovine serum was obtained from JRH Bioscience.

Example 1

Strategy for isolating cDNA clones for the mouse β3 subunit

Generation of a mouse β3 cDNA probe (mβ3 probe): This probe was generated using the following degenerate oligonucleotide primers:

5'-primer: CCA AGC TTG AC(A/C) T(G/C)T ACT A(C/T)C T(G/T)A TGG A

3'-primer: CCC TCG AGA A(A/G)T (C/T)GT CGC A(C/T)T CGC A(A/G)T A

The primers were designed based on a sequence which is highly conserved among all integrin β subunits (Ramaswamy & Hemler, 1990, *EMBO J.* 9: 1561–1568, which is incorporated by reference). Using polymerase chain reaction, a cDNA fragment of the β3 subunit was cloned from a cDNA library prepared from mouse osteoclasts. The identity of this mβ3 probe was confirmed by sequence analysis to be homologous to the published human β3 sequence (Frachet et al., 1990 *Mol. Biol. Rep.* 14:27–33, which is hereby incorporated by reference.).

Construction of a λZAP mouse osteoclast cDNA library (λZAP-OC)

The cDNA library was constructed from 5 µg polyA(+) RNA prepared from osteoclasts, which were generated from a co-culture of osteoblastic MB 1.8 cells and mouse bone marrow cells in the presence of 1,25-dihydroxy Vitamin $D_3$ (1,25(OH)2D3). Methods for generation and isolation of mouse osteoclasts from culture were performed as described by Tanaka, et al., 1991 *J. Bone Min. Res.* 6: S148, which is hereby incorporated by reference. The construction of this library was carried out according the instructions provided by the manufacturer, Stratagene (Lambda ZAP II Cloning Kits—236611). Random $pd(N)_6$ primers were used for the first strand cDNA synthesis.

Screening for mouse β3 clones: Mouse β3 cDNA clones were isolated by screening the primary λZAP-OC library ($0.5 \times 10^6$ pfu), using the mβ3 probe. Sixteen positive clones were isolated and rescued into pBluescript phagemid according to the manufacturer's protocol (Stratagene). These clones were initially characterized by restriction digestion with EcoRI to estimate the size of cDNA inserts. Clone 9A was found to be the largest (3.5 Kb) and was subsequently characterized by sequence analysis.

Cloning of 3'-cDNA fragment of mouse β3 by PCR: Clone 9A encodes for the entire sequence of mouse β3-trunc, which lacks only 121 amino acids (363 bp) from the expected C-terminus of β3-full, based on the published human β3 sequence. Therefore, the rest of the 3'-cDNA fragment was cloned by PCR. The following primers were used:

5'-primer (from BstEII site of clone 9A): TAA GGA CAG CCT CAC CGT CCA GGT

3'-primer (based on the human sequence): TCA TTA AGT CCT CGG TAC GTG ATA TTG GTG Full length mouse β3 cDNA was then constructed by ligating at the BstEII site between the clone 9A-derived 5'-fragment and the PCR clone-derived 3'-fragment.

RNA isolation and Northern blot analysis: Total cellular RNA was isolated by guanidine isothiocyanate and phenol extraction (Chomczynski & Sacchi, 1987, *Anal. Biochem.* 162:156–159.). Ten µg of total RNA was separated using formaldehyde-agarose gel electrophoresis, followed by transfer onto nylon filters (Hybond-N; Amersham). Poly A(+) RNA was prepared using QuickPrep mRNA Purification Kit (Pharmacia). Mouse tissue blots were purchased from Clontech. Mouse β3 specific probe was generated from the 5'-fragment of clone 9A using the EcoRI and BstEII sites. This probe can recognize both β3 full length and β3-trunc. Mouse β3-trunc specific probe was generated from the 3'-fragment of clone 9A using the Not I and EcoRI sites. Hybridizations were performed in 40% formamide, 5×SSC, 0.1% SDS, 0.1% ficoll, 0.1% polyvinylpyrolidone, 0.1% BSA and 200 mg/ml sonicated salmon sperm DNA at 42° C., overnight, and washed two times (30 min) at 55° C. in 0.1×SSC and 0.1% SDS. The filters were dried and exposed to XAR-2 films (Eastman Kodak, Rochester, N.Y.).

Example 2

Osteoclast Formation Assay

Osteoclast formation was determined using the mouse bone marrow-derived osteoblast co-culture system, as described by Takahashi, et al., 1988. In this assay, an osteoblastic cell line (MB1.8), established from neonatal mouse calvaria, were plated in 24-well culture dishes, at 10,000 cells per $cm^2$ in α-MEM containing 10% fetal bovine serum and 10 nM $1,25(OH)_2D_3$. Balb/C male mice (six weeks old) were sacrificed under CO2, and tibiae and femors were aseptically removed. The bone ends were cut off with scissors and the marrow cavity was flushed with 1 ml α-MEM by using a 27G needle. The bone marrow cells were then filtered through 70 µm nylon mesh. Cells were centrifuged for 7 min. at 300×g and washed once with α-MEM and finally resuspended and aliquoted at 25,000 cells/$cm^2$ onto the MB1.8 cells in the 24-well culture dishes. Medium with 10 nM 1,25(OH)2D3 was replaced every two days. Potential inhibitors of osteoclast formation were added to the cultures at day 2 and at day 4. After 7 days, the cultures were fixed and stained for Tartrate-resistance acid phosphatase (Trap) activity, essentially as described in Takahashi, et al., 1988. The formation of osteoclasts in this co-culture was quantitated as the number of multinucleated Trap(+) cells (with three or more nuclei) per well of a 24-well tissue culture plate.

Recombinant Expression of functional human integrin $\alpha_v\beta_3$ cDNAs for human $\alpha_V$ and human $\beta_3$ were cloned into pR135 and pCDNAI-neo expression vectors, both of which use the CMV promoter but contain hygromycin or neomycin resistance markers, respectively. Using these selection markers, we established a stable human embryonic kidney 293 cell line that stably expresses high levels of recombinant human $\alpha_V\beta_3$ was established. Surface expression of the receptor in this 293($\alpha_V\beta_3$) cell line were characterized using northern analysis, surface radioiodination followed by immunoprecipitation. In addition, the number of $\alpha_V\beta_3$) integrin receptors on the cell surface was estimated to be $1 \times 10^6$ receptor per cell, based on specific binding of $\alpha_V\beta_3$ to radio-iodinated echistatin.

Using the 293($\alpha_V\beta_3$) cell line, two different assays were developed for screening inhibitors of the integrin $\alpha_V\beta_3$: echistatin binding assay (EIB) and vitronectin cell attachment assay (VNADIN), below.

Echistatin Binding assay (EIB)

The membrane fraction of 293($\alpha_V\beta_3$) was solubilized in 100 mM octyl glucoside and the membrane protein extract is used in radio-iodinated echistatin binding. Binding buffer is 1% bovine serum albumin, 50 mM Tris-HCl (pH 7.2), 150 mM NaCl, 1 mM $CaCl_2$ and 1 mM $MgCl_2$. Membrane extract is incubated with radioiodinated echistatin (50,000 cpm), in the absence (total binding) or in the presence of unlabeled echistatin (specific binding) or in the presence of test compounds. Incubation period is 1 hour at room temperature. Specific echistatin bound proteins are filtered through a membrane using a Skatron Cell Harvester system.

Vitronectin Cell Attachment Assay (VNADIN)

96-well plates are coated with human vitronectin 293 ($\alpha_V\beta_3$) cells are lifted in trypsin/EDTA and washed in serum-free media. Cells are resuspended in attachment medium (Hank's balance salt containing BSA (1 mg/ml) and $CaCl_2$ (2 mM). Cells are then allowed to attach to vitronectin-coated wells for 1 hr at 37° C., in the absence (total attachment) or in the presence of tested compounds. Non-adhered cells are then removed by gently washing the wells with phosphate buffered saline.

The number of adhered cells can be quantitated by determining the relative levels of glucosaminidase activity overnight. The enzyme substrate solution is 3.75 mM p-nitrophenyl-N-acetyl-β-D-glucosaminide in 0.1M citrate buffer (pH 5.0) and 0.25% Triton X-100. The plates are incubated in the dark, room temperature, overnight. The color reaction is then developed by addition of 50 mM glycine, 5 mM EDTA at pH 10.5. Absorbance at O.D. 405 nm is determined and the number of cells can be quantitated using a standard curve of cells.

Assays using mouse β3

Essentially the same procedure is followed as described above to create a human embryonic kidney 293 cell line expressing either full-length mouse β3 or mouse β3 trunc. The EIB and/or VNADIN assays are then performed substantially as described, substituting the mouse β3 or mouse β3-trunc expressing cells.

What is claimed is:

1. cDNA encoding mouse integrin β3-trunc subunit as shown in SEQ ID NO:2, cDNA being free from associated mouse nucleic acid.

2. A vector comprising the cDNA of claim 1.

3. A host cell comprising the vector of claim 2.

4. A method for making mouse β3-trunc comprising transforming a host cell with a vector comprising the cDNA of claim 1 and harvesting the β3-trunc so produced.

* * * * *